United States Patent [19]

Wong et al.

[11] Patent Number: 4,547,324
[45] Date of Patent: Oct. 15, 1985

[54] METHOD FOR PREPARATION OF N-PHOSPHONOMETHYLGLYCINE

[75] Inventors: Rayman Y. Wong, Richmond; Nathan S. Bunker, El Cerrito, both of Calif.

[73] Assignee: Stauffer Chemical Company, Westport, Conn.

[21] Appl. No.: 635,033

[22] Filed: Jul. 27, 1984

Related U.S. Application Data

[63] Continuation of Ser. No. 403,238, Jul. 29, 1982, abandoned.

[51] Int. Cl.$^4$ ............................................. C07F 9/38
[52] U.S. Cl. ........................... 260/502.4 R; 548/112; 548/229; 71/86
[58] Field of Search .......................... 548/112, 229; 260/502.4 R

[56] References Cited

U.S. PATENT DOCUMENTS 4,128,558  12/1978  Hendricks et al. ................. 548/112
4,374,131   2/1983  Petrillo ........................... 548/112 X

OTHER PUBLICATIONS

Kosolapoff et al., Organic Phosphorus Compounds, vol. 7, Wiley-Interscience, New York, (1976), pp. 7 & 8.

*Primary Examiner*—Richard L. Raymond
*Attorney, Agent, or Firm*—Paul R. Martin

[57] ABSTRACT

A method for the production of N-phosphonomethylglycine which comprises reacting a 2-oxazolidone starting compound of the formula

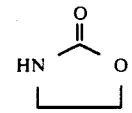

with p-formaldehyde, then adding a substituted phosphorus compound of the formula PXYZ wherein X is halogen, and Y and Z are independently selected from the group consisting of halogen, alkoxy having from 1-10 carbon atoms, and aryloxy, said reaction being conducted in the presence of a low molecular weight carboxylic acid solvent for the reactants, at a combination of time and temperature sufficient to cause the reaction to go to completion, and converting the 2-oxo-3-oxazolidinyl methyl phosphonic acid thus formed to N-phosphonomethylglycine.

4 Claims, No Drawings

METHOD FOR PREPARATION OF N-PHOSPHONOMETHYLGLYCINE

This is a continuation, of application Ser. No. 403,238, filed July 29, 1982, now abandoned.

BACKGROUND OF THE INVENTION

This invention relates to a novel method for the preparation of N-phosphonomethylglycine, a compound which is a known herbicide and plant growth regulator.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and post-emergence herbicides. The pre-emergence herbicides are normally incorporated into the soil prior to the emergence of the weed plants from the soil, and the post-emergence herbicides are normally applied to plant surfaces after emergence of the weeds or other unwanted plants from the soil.

One of the earliest post-emergence herbicides used commercially was 2,4-D (2,4dichlorophenoxyacetic acid). After a number of years of use of this and similar compounds such as 2,4,5-T (2,4,5-trichlorophenoxy acetic acid), it was found that certain decomposition products of these herbicides were long lasting and were not biodegradable. While there has been some dispute between governmental agencies and commercial interests regarding the effects of residual products of 2,4-D, 2,4,5-T and similar compounds, the agencies nevertheless restricted the use of these herbicides in the United States some years ago. Since that time, efforts have beem made to develop herbicides which are biodegradable into harmless residues within a relatively short time after their application.

One such compound, which has been found to be diodegradable, yet which is effective as a herbicide and plant growth regulator when employed at lower rates, is N-phosphonomethylglycine and various salts thereof.

In field use it is normally applied in amounts of from 0.01 to about 20 pounds per acre, preferably from 2 to 6 pounds per acre.

The N-phosphonomethylglycines, and certain soluble salts thereof, can be made in a number of different ways. One such method, as described in U.S. Pat. No. 3,160,632 (Toy et al., Dec. 8, 1964) is to react N-phosphinomethylglycine (glycinemethylenephosphinic acid) with mercuric chloride in a water solvent at reflux temperature, and subsequently separating the reacton products. Other methods include the phosphonomethylation of glycine and the reaction of ethyl glycinate with formaldehyde and diethylphosphite. The latter method is described in U.S. Pat. No. 3,799,758 (Franz, Mar. 26, 1974). In addition, there is a whole series of patents, relating to N-phosphonomethylglycines, their salts, and derivatives thereof, described as being useful herbicides and plant growth regulators. Such additional patents relating to the N-phosphonomethylglycines, methods of application, methods of preparation, salts, and derivatives, include U.S. Pat. No. 3,868,407, U.S. Pat. No. 4,197,254, and U.S. Pat. No. 4,199,354, among others.

Because of the importance of N-phosphonomethylglycine and certain salts as a herbicide, other methods of making the compounds are constantly being sought in order to provide improved and alternate methods of manufacture.

The subject invention is thus concerned with a process for the preparation of N-phosphonomethylglycine, and intermediates in that process, which intermediates are new compositions of matter used in the ultimate production of the N-phosphonomethylglycine referred to above.

SUMMARY OF THE INVENTION

The process of the invention comprises three separate steps. The first step involves the preparation of the intermediate 2-oxo-3oxa-zolidinylmethyl phosphonic acid, from a 2-oxazolidine starting compound, subsequent conversion of the 2-oxo-3-oxazolidinylmentyl phosphonic acid intermediate to a salt form of N-phosphonomethylglycine, then acidifying the salt to N-phosphonomethylglycine.

The process comprises (1) first reacting 2-oxazolidine with p-formaldehyde, then adding to the reaction solution a substituted phosphorus compound of the formula PXYZ wherein X is a halogen atom, and Y and Z are independently selected from the group consisting of halogen, alkoxy having from 1–10 carbon atoms and aryloxy, the reaction being conducted in the presence of a low molecular weight carboxylic acid solvent, and with a combination of time, temperature and pressure sufficient to cause formation of an intermediate product, 2-oxo-3-oxazolidinylmethyl phosphonic acid, (2) reaction of the 2-oxo-3-oxazolidinylmethyl phosphonic acid, with an alkali or alkaline earth base in an aqueous solvent medium, and using cadmium oxide as a catalyst, the reaction being conducted at a combination of time, temperature and pressure sufficient to cause formation of a salt of N-phosphonomethylglycine, and (3) acidifying the salt with an acid resulting in the concurrent evolution of carbon dioxide and production of N-phosphonomethyglycine.

The intermediate compound produced in accordance with step (1) of the process, 2-oxo-3-oxazolidinylmethyl phosphonic acid, is a new composition of matter, characterized by a combination of mass infrared, H'-NMR, and $^{13}$-NMR spectra. It has the formula

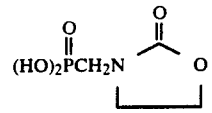

The reaction temperature for the first step of the reaction will normally range from about 25 to about 118° C. and preferably from about 90 to about 118° C. The reaction is conventionally conducted at atmospheric pressure.

The preferred substituted phosphorus compound is phosphorus trichloride.

It has been found that the process of the invention is workable only when the formaldehyde is water-free. Thus, the only formaldehyde which will work in the process is para-formaldehyde. The p-formaldehyde (CH₂O)$_n$ serves to hydroxymethylate the starting material in the first step of the reaction of the invention.

In carrying out step (1) of the process, the 2-oxazolidinone and p-formaldehyde are first added together with mixing, in the presence of the carboxylic acid solvent, and the reaction solution is heated to reflux temperature. After a period of time, the solution is then cooled to approximately room temperature and the substituted phosphorus compound is then added. The reason for this is that were the substituted phosphorus compound to be added at reflux temperature, a violent reaction might occur liberating copious amounts of HCl, thus it is necessary to cool the solution to such an extent that the substituted phosphorus compound can be added without deleterious results. After the phosphorus compound has been added, however, the temperature is again raised to reflux, which, if glacial acetic acid is used as a solvent, is approximately 118° C.

Water is added at the end of step (1). The purpose of the addition of water is to create the decomposition of one of the by-products of the process, bis-chloromethyl ether, which is known to be a carcinogen. The water has the effect of splitting the carcinogen into two innocuous by-products.

The mole ratio of starting compound to p-formaldehyde to phosphorus trichloride or other phosphorus substituted compound preferably ranges from about 1:1:1 to about 1:1.2:1.2, with the most preferred ratio from 1:1:1.

While glacial acetic acid is the solvent of choice for the reactants, other solvents can be used, such as any other low molecular weight carboxylic acid, as for example, propanoic and butanoic acid.

Step (2) of the process of the invention involves the reaction of the 2-oxo-3-oxazolidinyl methyl phosphonic acid with an alkali or alkaline earth base in order to neutralize the phosphonic acid and hydrolyze the oxazolidone ring to the corresponding open chain alcohol. Preferred bases are sodium hydroxide and potassium hydroxide, although any other alkali or alkaline earth base can be used. The above alcohol is then oxidized to the corresponding carboxylic acid in the presence of cadmium oxide catalyst and water.

The second step of the reaction is carried out in an aqueous medium, and for these purposes, water is the solvent of choice.

Cadmium oxide has been determined to be the only catalyst which is suitable for use in this step of the reaction.

The reaction is preferably carried out under pressure and when sodium hydroxide is the base the pressure can range from about 500 psi to about 2000 psi.

The reaction is also conducted with heat and the temperature range for the reaction, again when sodium hydroxide is used as the preferred base, can range from about 220° to about 300° C.

The third step in the process of the invention involves the acidification of the salt of N-phosphonomethylglycine with a mineral acid. Practically any mineral acid can be used, however, the preferred acid is hydrochloric acid. Other acids which also are suitable include sulfuric acid, hydriodic acid, and others of the same general type. This step can be conducted at room temperature, or below, with the preferred range being from about 0° to about 5° C.

In each instance, of steps (1), (2) or (3), the reaction is carried out at a sufficient period of time to allow completion of the reaction. This time will vary in accordance with the particular reactants used. In the case of the preferred reactants, the first step of the process takes about 4 hours, the second step of the process takes about 6 hours and the third step about 10 minutes.

It will be appreciated by those skilled in the art that the specific reaction times, temperature, and pressure can be varied without departing from the spirit and scope of the invention.

This invention will be better understood by reference to the specific examples which follow, which serves to illustrate the method of the instant invention.

EXAMPLE 1

Preparation of 2-Oxo-3-oxazolidinyl Methyl Phosphonic Acid

A 500 milliliter (ml), three-necked, round-bottom flask was obtained and equipped with a magnetic stirring bar, a stopper, an argon inlet, and a condenser connected to a 10% sodium hydroxide acid-scrubber, and to this flask was added 20.0 grams (g) (0.23 moles) of 2-oxazolidinone, 6.9 g para-formaldehyde (MCB) and 120 g of glacial acetic acid. A white suspension formed, and this suspension was heated to reflux temperature and refluxed for 45 minutes.

The solution then cleared, and the clear, colorless solution was cooled to room temperature, then 31.6 g of phosphorus trichloride was added with stirring over a period of 1 minute via an addition funnel. During and after the addition, hydrogen chloride evolved. The reaction mixture was then warmed to reflux temperature again and refluxed for 2.0 hours. Thereafter, 130 ml of water (distilled) was added to the refluxing solution and the solution refluxed for an additional 1.5 hours. The product in solution was then cooled to room temperature and the solvent removed in vacuo. The product remaining in the flask was a clear, faintly yellow oil (46 g) having $n_D^{30}$ 1.4822, which crystallized to a soft solid on standing.

EXAMPLE 2

Preparation of 2-Oxo-3-oxazolidinyl Methyl Phosphonic Acid

A 2000 ml, three-necked, round-bottom flask was obtained and equipped with a magnetic stirring bar, an addition funnel, an argon inlet, and a condenser connected to a 10% sodium hydroxide scrubber. To the flask was added 100 g (1.2 mole) of 2-oxazolidinone, 38 g (1.2 mole) of p-formaldehyde, and 600 g of glacial acetic acid. A white suspension formed and this suspension was then heated to reflux temperature and held there for 45 minutes, after which time the reaction mixture was a clear, colorless solution. The solution was then cooled to room temperature and while stirring, 174 g of phosphorus trichloride was added over a period of approximately 20 minutes. Heat evolved and the solution turned a light yellow color with concomitant formation of copious amounts of HCl. The reaction solution was then heated to reflux temperature and held there for 3 hours. To this solution was added 500 ml of distilled water, and that mixture was then reheated to reflux and held there for an additional 1 hour. The reaction solution was cooled to room temperature, and the solvent removed in vacuo, leaving 247 g of a light, clear yellow oil, determined by suitable analytic techniques to be the subject compound. The oil crystallized to a soft solid on standing.

EXAMPLE 3

Preparation of N-Phosphonomethylglycine

A quantity of 2-oxo-3-oxazolidinylmethyl phosphonic acid was prepared in accordance with the method described in Example 1 above.

To a 300 ml stainless steel autoclave equipped with a magnetic stirrer, a thermal couple sensor, and a pressure gauge, was introduced a solution of 17.3 g (0.10 mole) of 2-oxo-3-oxazolidinylmethyl phosphonic acid and 20 g (0.50 mole) of sodium hydroxide in 100 ml of water. To the clear, almost colorless solution thus formed, was added 1.3 g (0.01 mole) of cadmium oxide, and the vessel was sealed and pressure tested to 2000 psi. The reactants were then heated to 260° C. and maintained at that temperature for one hour and the pressure in the autoclave was 680 psi. The heat was then turned off and the reactants allowed to cool slowly.

The vessel was completely depressurized and an $C^{13}$ nmr of the contents taken. It was determined that the sodium salt N-phosphonomethylglycine was present. The clear basic solution was then cooled to 0° C. and carefully decarboxylated by adding 45 ml of concentrated hydrochloric acid. At this time copious gas evolution resulted. The clear, brown solution was seeded with a few crystals of N-phosphonomethylglycine and allowed to stand in the cold overnight. The next day, the solution was analyzed by high pressure liquid chromatography (hplc) which revealed the presence of a small amount of N-phosphonomethylglycine.

The N-phosphonomethylglycine which is produced from the intermediate 2-oxo-3-oxazolidinylmethylphosphonic acid, made in accordance with the method of the invention, in and of itself, has herbicidal and plant growth regulating efficacy. However, because the acid is not in itself very soluble in aqueous solutions, it is preferred to convert the compound to its salt form for inclusion into herbicidal compositions. Salt forms which have been found to have high rates of herbicidal activity and plant growth regulating activity are the trialkylsulfonium salts of N-phosphonomethylglycine, such as are disclosed in U.S. Pat. No. 4,315,765.

It will be appreciated by those skilled in the art that variations in times, temperatures, pressures, and the like can be had in the process described without departing from the spirit of the invention and the scope of the claims herein.

What is claimed is:

1. A method for the preparation of N-phosphonomethylglycine which comprises the steps of
   (1) reacting a starting compound of the formula

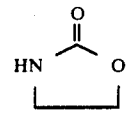

with p-formaldehyde, then adding a substituted phosphorus compound of the formula PXYZ wherein X is halogen, and Y and Z are independently selected from the group consisting of halogen, alkoxy having from 1–10 carbon atoms and aryloxy, said reaction being conducted in the presence of a low molecular weight carboxylic acid solvent for the reactants, at a combination of time and temperature sufficient to cause the formation of an intermediate 2-oxo-3-oxazolidinyl methyl phosphonic acid,
   (2) reacting said 2-oxo-3-oxazolidinylmethyl phosphonic acid with an alkali or alkaline earth hydroxide, and cadmium oxide catalyst in water, and
   (3) subsequently acidifying the reactants with an acid to form the end product N-phosphonomethylglycine.

2. The method of claim 1 in which the mole ratio of 2-oxazolidine to para-formaldehyde to substituted phosphorous compound ranges from about 1:1:1 to about 1:1.2:1.2.

3. The method of claim 1 in which the reaction is carried out at atmospheric pressure.

4. The method of claim 1 in which the phosphorus substituted compound is phosphorus trichloride.

* * * * *